US012064133B2

(12) United States Patent
Magno, Jr.

(10) Patent No.: US 12,064,133 B2
(45) Date of Patent: Aug. 20, 2024

(54) TISSUE RESECTION DEVICE

(71) Applicant: Gyrus ACMI, Inc., Southborough, MA (US)

(72) Inventor: Joey Magno, Jr., Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 674 days.

(21) Appl. No.: 16/935,367

(22) Filed: Jul. 22, 2020

(65) Prior Publication Data

US 2020/0345386 A1 Nov. 5, 2020

Related U.S. Application Data

(63) Continuation of application No. 15/727,697, filed on Oct. 9, 2017, now Pat. No. 10,751,077.

(51) Int. Cl.
*A61B 17/32* (2006.01)
*A61B 10/02* (2006.01)
(Continued)

(52) U.S. Cl.
CPC .. *A61B 17/320016* (2013.01); *A61B 10/0291* (2013.01); *A61B 17/32002* (2013.01);
(Continued)

(58) Field of Classification Search
CPC ... A61B 17/320016–32002; A61B 17/320758; A61B 17/42; A61B 17/29; A61B 2217/005; A61B 17/3207
See application file for complete search history.

(56) References Cited

U.S. PATENT DOCUMENTS 4,306,570 A * 12/1981 Matthews ............ A61B 10/025
600/568
5,618,293 A * 4/1997 Sample ............ A61B 17/32002
606/180
(Continued)

FOREIGN PATENT DOCUMENTS

CN 109620358 A 4/2019
DE 102007023207 A1 11/2008
(Continued)

OTHER PUBLICATIONS

"European Application Serial No. 18197813.1, Response filed Jan. 6, 2021 to Summons to Attend Oral Proceedings mailed Aug. 21, 2020", 52 pgs.
(Continued)

*Primary Examiner* — Darwin P Erezo
*Assistant Examiner* — Brigid K Byrd
(74) *Attorney, Agent, or Firm* — Schwegman Lundberg & Woessner, P.A.

(57) ABSTRACT

A medical device includes an outer tubular member, a middle tubular member received within the outer tubular member, an inner tubular member received within the middle tubular member, and an engagement gear, wherein the inner tubular member is configured to be rotatable in one direction while the middle tubular member is configured to be simultaneously rotatable in an opposite direction through the engagement gear while the outer tubular member is configured to be stationary relative to both the middle tubular member and the inner tubular member.

15 Claims, 7 Drawing Sheets

(51) Int. Cl.
*A61B 17/3205* (2006.01)
*A61B 17/3207* (2006.01)
*A61B 17/30* (2006.01)
*A61B 17/42* (2006.01)
*A61B 18/00* (2006.01)

(52) U.S. Cl.
CPC .............. *A61B 17/32056* (2013.01); *A61B 17/320758* (2013.01); *A61B 2017/306* (2013.01); *A61B 2017/4216* (2013.01); *A61B 2018/00559* (2013.01); *A61B 2217/005* (2013.01)

(56) References Cited

U.S. PATENT DOCUMENTS

| | | | |
|---|---|---|---|
| 10,363,066 B2 | 7/2019 | Magno | |
| 10,751,077 B2 | 8/2020 | Magno | |
| 2004/0010258 A1* | 1/2004 | Carusillo | A61M 1/77 606/79 |
| 2010/0204722 A1* | 8/2010 | Gilsdorf | A61B 17/42 606/170 |
| 2014/0100567 A1* | 4/2014 | Edwards | A61B 17/32002 606/45 |
| 2014/0277036 A1* | 9/2014 | Flynn | A61B 17/3205 606/170 |
| 2017/0027611 A1 | 2/2017 | Adams | |
| 2019/0105071 A1 | 4/2019 | Magno, Jr. | |
| 2019/0290327 A1 | 9/2019 | Magno | |

FOREIGN PATENT DOCUMENTS

| | | | |
|---|---|---|---|
| EP | 3 466 355 A1 | 4/2019 | |
| EP | 3466355 B1 | 8/2021 | |
| JP | 2019069141 A | 5/2019 | |
| WO | WO-2014/133664 A1 | 9/2014 | |

OTHER PUBLICATIONS

"European Application Serial No. 21190203.6, Extended European Search Report mailed Jan. 10, 2022", 8 pgs.
U.S. Appl. No. 15/727,697, now U.S. Pat. No. 10,751,077, filed Oct. 9, 2017, Tissue Resection Device.
"U.S. Appl. No. 15/727,697, Non Final Office Action mailed Jan. 22, 2020", 19 pgs.
"U.S. Appl. No. 15/727,697, Notice of Allowance mailed Apr. 29, 2020", 9 pgs.
"U.S. Appl. No. 15/727,697, Response filed Apr. 13, 2020 to Non Final Office Action mailed Jan. 22, 2020", 13 pgs.
"U.S. Appl. No. 15/727,697, Response filed Oct. 28, 2020 to Restriction Requirement mailed Sep. 3, 2019", 2 pgs.
"U.S. Appl. No. 15/727,697, Restriction Requirement mailed Sep. 3, 2019", 6 pgs.
"European Application Serial No. 18197813.1, Communication Pursuant to Article 94(3) EPC mailed Jan. 14, 2020", 5 pgs.
"European Application Serial No. 18197813.1, Extended European Search Report mailed Feb. 12, 2019", 8 pgs.
"European Application Serial No. 18197813.1, Response filed Apr. 28, 2020 to Communication Pursuant to Article 94(3) EPC mailed Jan. 14, 2020", 52 pgs.
"European Application Serial No. 18197813.1, Response filed May 10, 2019 to Extended European Search Report mailed Feb. 12, 2019", 7 pgs.
"European Application Serial No. 18197813.1, Summons to Attend Oral Proceedings mailed Aug. 21, 2020", 5 pgs.
"European Application Serial No. 21190203.6, Response filed Aug. 5, 2022 to Extended European Search Report mailed Jan. 10, 2022", 7 pgs.

* cited by examiner

TISSUE RESECTION DEVICE

CROSS REFERENCE

This patent application is a continuation application of copending U.S. patent application Ser. No. 15/727,697, filed on Oct. 9, 2017, the disclosure of which is incorporated by reference herein in its entirety.

FIELD

The present disclosure relates generally to a tissue resection device. More particularly, the disclosure relates to a tissue resection blade assembly.

BACKGROUND

Conventional tissue resection devices participate in the treatment of resecting sub-mucosal non-cancerous growth of polyps and fibroid tissues in the uterine cavity. The areas where these unwanted tissues grow can be anywhere on the endometrium surfaces of the uterus and on the inside wall of the fundus on the upper third of the uterus.

Many of the resection devices with the conventional configurations require multiple blades. These conventional configurations generally comprise one or more dedicated blades for resecting hard to reach areas, and another dedicated blade for resecting larger and harder tissues.

Accordingly, as the conventional configurations generally result in various limitations and disadvantages, there is a need to provide improved and reliable configurations for tissue cutting devices.

SUMMARY

In an embodiment, the present disclosure provides a medical device comprising: an outer tubular member; a middle tubular member configured to be received within the outer tubular member; an inner tubular member configured to be received within the middle tubular member; and an engagement gear configured to engage both the middle tubular member and the inner tubular member, wherein the inner tubular member is configured to be rotatable in one direction while the middle tubular member is configured to be simultaneously rotatable in an opposite direction through the engagement gear.

In an embodiment, the present disclosure provides a medical device comprising: an outer tubular member having a proximal end and a distal end; a middle tubular member having a proximal end, a distal end, and a beveled gear disposed at the proximal end, the middle tubular member configured to be received within the outer tubular member; an inner tubular member having a proximal end, a distal end, and a beveled gear disposed at the proximal end, the inner tubular member configured to be received within the middle tubular member; and an engagement gear configured to engage the beveled gear of the middle tubular member and the beveled gear of the inner tubular member, wherein the inner tubular member is configured to be rotatable in one direction while the middle tubular member is configured to be simultaneously rotatable in an opposite direction through the engagement gear.

In an embodiment, the present disclosure provides a medical device comprising: an outer tubular member having a proximal end and a distal end; a middle tubular member having a proximal end, a distal end, and a beveled gear disposed at the proximal end, the middle tubular member configured to be received within the outer tubular member; an inner tubular member having a proximal end, a distal end, and a beveled gear disposed at the proximal end, the inner tubular member configured to be received within the middle tubular member; and an engagement gear configured to engage the beveled gear of the middle tubular member and the beveled gear of the inner tubular member, wherein the inner tubular member is configured to be rotatable in one direction while the middle tubular member is configured to be simultaneously rotatable in an opposite direction through the engagement gear, and wherein the outer tubular member is configured to remain stationary relative to both the inner tubular member and the middle tubular member during an operation.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage both the beveled gear of the middle tubular member and the beveled gear of the inner tubular member, wherein the opening of the middle tubular member and the opening of the inner tubular member are configured to form a cutting tool when the inner tubular member and the middle tubular member rotate in opposite directions through the engagement gear while the outer tubular member is configured to remain stationary.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage the beveled gear of the middle tubular member and the beveled gear of the inner tubular member, wherein the opening of the middle tubular member and the opening of the inner tubular member are configured to form a cutting tool when the two openings are aligned or superimposed with the open window of the outer tubular member.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage the beveled gear of the middle tubular member and the beveled gear of the inner tubular member, wherein the distal end of the middle tubular member is configured to form a closed configuration with the distal end of the outer tubular member such that no liquid can flow through the open window of the outer tubular member or the opening of the middle tubular member when the device is in its resting configuration or when the device is power off.

DETAILED DESCRIPTION

Figure 1:
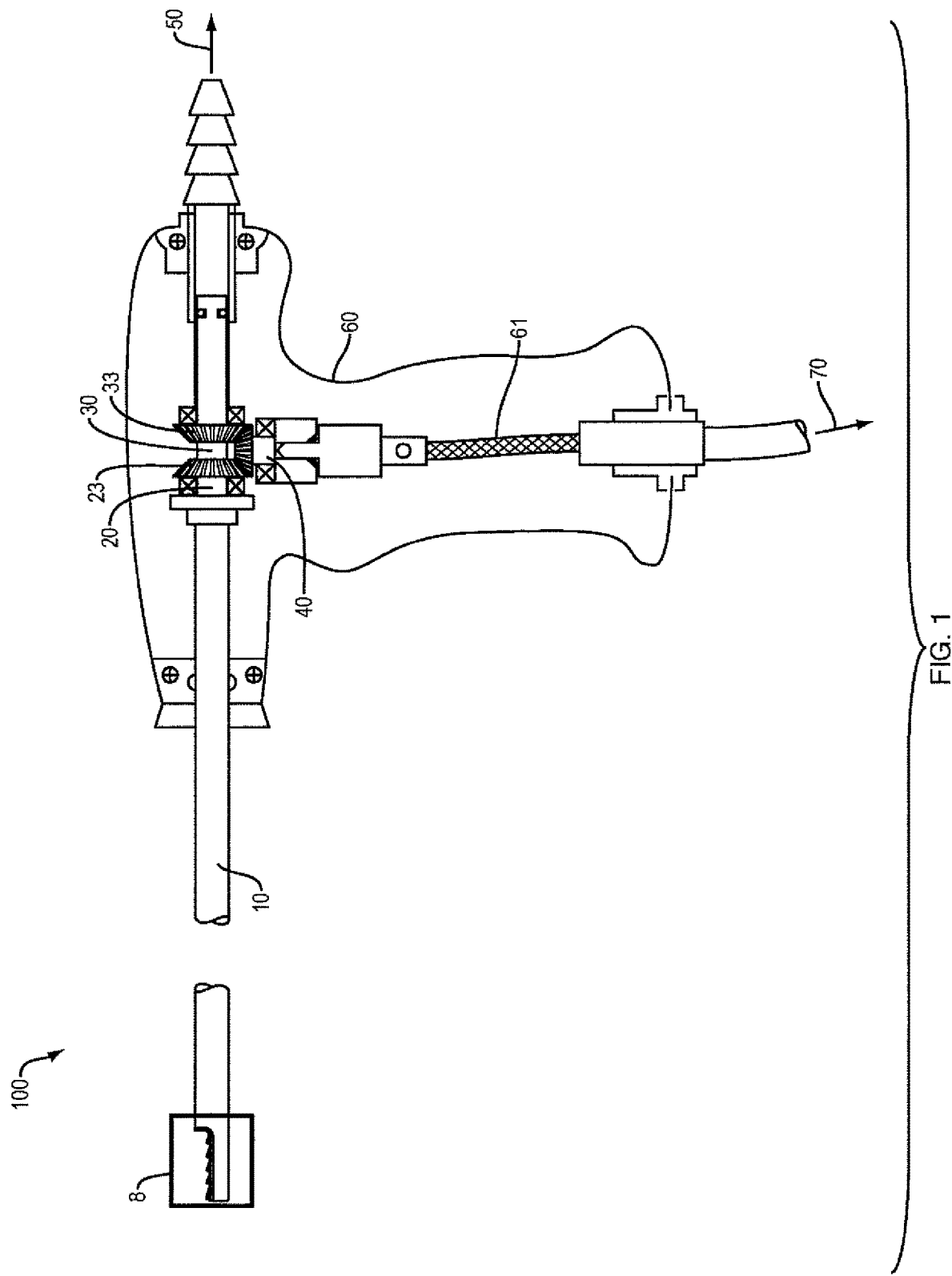
FIG. 1 is a partial schematic view of a medical device in accordance with one aspect of the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", "above embodiment", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" in connection with a range applies to both ends of the range. Thus, "about 10 to 30" is intended to cover "about 10 to about 30", inclusive of at least the specified endpoints.

In an embodiment, the present disclosure provides a medical device. The medical device includes an outer tubular member, a middle tubular member, an inner tubular member, and an engagement gear. The outer tubular member has a proximal end and a distal end. The middle tubular member has a proximal end and a distal end. The middle tubular member is configured to be received within the outer tubular member and capable of being rotatable relative to the outer tubular member. The inner tubular member has a proximal end and a distal end. The inner tubular member is configured to be received within the middle tubular member and capable of being rotatable relative to the outer tubular member. The inner tubular member is configured to be rotatable in one direction while the middle tubular member is configured to be simultaneously rotatable in an opposite direction. The outer tubular member is configured to remain stationary relative to the inner tubular member and the middle tubular member while the inner tubular member and the middle tubular member are rotating.

In an embodiment, the present disclosure provides a medical device comprising: an outer tubular member; a middle tubular member configured to be received within the outer tubular member; an inner tubular member configured to be received within the middle tubular member; and an engagement gear configured to engage both the middle tubular member and the inner tubular member, wherein the inner tubular member is configured to be rotatable in one direction while the middle tubular member is configured to be simultaneously rotatable in an opposite direction through the engagement gear. In an embodiment, the inner tubular member is configured to be connectable to an electrical motor. In an embodiment, the inner tubular member is configured to be connectable to a suction source. In an embodiment, the outer tubular member is configured to remain stationary relative to the inner tubular member and the middle tubular member during an operation. In an embodiment, the engagement gear is configured to be connectable to an electrical motor. In an embodiment, the engagement gear is configured to be connectable to a motor control box. In an embodiment, the engagement gear is configured to be connectable to a power source. In an embodiment, the power source is a battery pack.

In an embodiment, the present disclosure provides a medical device comprising: an outer tubular member having a proximal end and a distal end; a middle tubular member having a proximal end, a distal end, a beveled gear disposed at the proximal end, the middle tubular member configured to be received within the outer tubular member; an inner tubular member having a proximal end, a beveled gear disposed at the proximal end, and a distal end, the inner tubular member configured to be received within the middle tubular member; and an engagement gear configured to engage the beveled gear of the middle tubular member and the beveled gear of the inner tubular member, wherein the inner tubular member is configured to be rotatable in one direction while the middle tubular member is configured to be simultaneously rotatable in an opposite direction through the engagement gear. In an embodiment, the inner tubular member is configured to be connectable to an electrical motor. In an embodiment, the inner tubular member is configured to be connectable to a suction source. In an embodiment, the outer tubular member is configured to remain stationary relative to the inner tubular member and the middle tubular member during an operation. In an embodiment, the engagement gear is configured to be connectable to an electrical motor. In an embodiment, the engagement gear is configured to be connectable to a motor control box. In an embodiment, the engagement gear is configured to be connectable to a power source. In an embodiment, the power source is a battery pack.

In an embodiment, the present disclosure provides a medical device for cutting tissue. The device includes an outer tubular member, a middle tubular member, an inner tubular member, and a engagement gear. The outer tubular member has a proximal end, a distal end, and an open window disposed at the distal end. The middle tubular member has a proximal, a beveled gear disposed at the proximal end, a distal end, and an opening disposed at the distal end. The middle tubular member is configured to be received within the outer tubular member. The inner tubular member has a proximal end, a beveled gear disposed at the proximal end, a distal end, an opening disposed at the distal end. The inner tubular member is configured to be received within the middle tubular member. The engagement gear is configured to engage both the beveled gear of the middle tubular member and the beveled gear of the inner tubular member. The opening of the middle tubular member is configured to align or superimpose with the open window of the outer tubular member. The opening of the inner tubular member is configured to align or superimpose with the open window of the outer tubular member. The opening of the middle tubular member is configured to align or superimpose with the opening of the inner tubular member. The opening of the middle tubular member and the opening of the inner tubular member are configured to form a cutting tool when the inner tubular member and the middle tubular member rotate in opposite directions during an operation. The inner tubular member is configured to be rotatable in one direction while the middle tubular member is configured to be simultaneously rotatable in an opposite direction. The outer tubular member is configured to remain stationary while the inner tubular member and the middle tubular member are rotating.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage the beveled gear of the middle tubular member and the beveled gear of the inner tubular member, wherein the opening of the middle tubular member and the opening of the inner tubular member are configured to form a cutting tool when the openings of the inner tubular member and the middle tubular member are aligned or superimposed with the open window of the outer tubular member. In an embodiment, the inner tubular member is configured to be connectable to an electrical motor. In an embodiment, the inner tubular member is configured to be connectable to a suction source. In an embodiment, the outer tubular member is configured to remain stationary relative to the inner tubular member and the middle tubular member during an operation. In an embodiment, the engagement gear is configured to be connectable to an electrical motor. In an embodiment, the engagement gear is configured to be connectable to a motor control box. In an embodiment, the engagement gear is configured to be connectable to a power source. In an embodiment, the power source is a battery pack.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage the beveled gear of the middle tubular member and the beveled gear of the inner tubular member, wherein the opening of the middle tubular member and the opening of the inner tubular member are configured to form a cutting tool when the inner tubular member and the middle tubular member rotate in opposite directions through the engagement gear. In an embodiment, the inner tubular member is configured to be connectable to an electrical motor. In an embodiment, the inner tubular member is configured to be connectable to a suction source. In an embodiment, the outer tubular member is configured to remain stationary relative to the inner tubular member and the middle tubular member during an operation. In an embodiment, the engagement gear is configured to be connectable to an electrical motor. In an embodiment, the engagement gear is configured to be connectable to a motor control box. In an embodiment, the engagement gear is configured to be connectable to a power source. In an embodiment, the power source is a battery pack.

In an embodiment, the present disclosure provides a medical device for cutting tissue, the device comprising: an outer tubular member having a proximal end, a distal end, and an open window disposed at the distal end; a middle tubular member having a proximal end, a beveled gear disposed at the proximal end, a distal end, and an opening disposed at the distal end, the middle tubular member configured to be received within the outer tubular member; an inner tubular member having a proximal end, a beveled gear disposed at the proximal end, a distal end, and an opening disposed at the distal end, the inner tubular member configured to be received within the middle tubular member; and an engagement gear configured to engage the beveled gear of the middle tubular member and the beveled gear of the inner tubular member, wherein the distal end of the middle tubular member is configured to form a closed configuration with the distal end of the outer tubular member such that no liquid can flow through the open window of the outer tubular member or the opening of the middle tubular member when the medical device is in its resting position or power off. In an embodiment, the inner tubular member is configured to be connectable to an electrical motor. In an embodiment, the inner tubular member is configured to be connectable to a suction source. In an embodiment, the outer tubular member is configured to remain stationary relative to the inner tubular member and the middle tubular member during an operation. In an embodiment, the engagement gear is configured to be connectable to an electrical motor. In an embodiment, the engagement gear is configured to be connectable to a motor control box. In an embodiment, the engagement gear is configured to be connectable to a power source. In an embodiment, the power source is a battery pack.

In the above embodiments, the outer tubular member includes a proximal end, a distal end, and an open window disposed at the proximal end. In these embodiments, the outer tubular member may be configured to have an inner diameter (I.D.) of about 0.20 to about 0.30 inch, preferably about 0.21 to about 0.24 inch, even more preferably about 0.22 or about 0.222 inch. It may be configured to have an outer diameter (O.D.) of about 0.20 to about 0.30 inch, preferably about 0.23 to about 0.25 inch, even more preferably about 0.24 or about 0.242 inch. Its length may be configured to be about 12.00 to about 16.00 inch, preferably about 13.00 to about 15.00 inch, even more preferably about 14.00 inch. The open window of the outer tubular member may be preferably configured to be disposed at the farthest distal end. The open window may be configured to have a length of about 0.20 to about 0.50 inch, preferably about 0.30 to about 0.40 inch, even more preferably about 0.37, or about 0.38, or about 0.39 inch along its longitudinal axis direction. The open window may be preferably configured to have smooth edges even though other suitable types are contemplated. The outer tubular member may be made of metal, stainless steel or other suitable materials strong enough for performing the desired functions. It may be made reusable, autoclavable, or disposable.

In the above embodiments, the middle tubular member includes a proximal end, a beveled gear disposed at the proximal end, a distal end, and an opening disposed at the distal end. The middle tubular member may be configured to have an inner diameter (I.D.) of about 0.15 to about 0.25 inch, preferably about 0.18 to about 0.22 inch, even more preferably about 0.20 or about 0.202 inch. It may be configured to have an outer diameter (O.D.) of about 0.20 to about 0.30 inch, preferably about 0.21 to about 0.24 inch, even more preferably about 0.22 or about 0.222 inch. Its length may be configured to be about 13.00 to about 17.00 inch, preferably about 14.00 to about 16.00 inch, even more preferably about 15.00 inch. The opening of the middle tubular member may be configured to be disposed at the farthest distal end. The opening may be configured to have a length of about 0.20 to about 0.50 inch, preferably about 0.30 to about 0.40 inch, even more preferably about 0.36, or about 0.37, or about 0.38 inch along its longitudinal axis direction. One side of the opening is configured to have serrations, sharp teeth, knife edges, or other types of edges suitable for performing cutting functions. The serration, the tooth, or the knife edge of the opening has an outside surface edge and an inside surface edge. The outside surface edge may be preferably configured to be sharper than the inside surface edge for more efficient cutting purpose when aligned with the opening of the inner tubular member. Other sides may be configured to be smooth or other suitable edges. The beveled gear is configured to fully align with the engagement gear. It may be made whole with the middle tubular body, or it may be made separately and attached to the tubular body through means such as snap fit, screw tight, and high power glue known in the art. The middle tubular member is configured to synchronize with the inner tubular member to achieve tissue cutting along the middle axis of the open window of the outer tubular member through means known in the art. The middle tubular member may be configured to be rotatable clockwise. The middle tubular member may be configured to be rotatable counter clockwise. The middle tubular member may be made of metal, stainless steel or other suitable materials strong enough for performing the desired functions. It may be made reusable, autoclavable, or disposable.

In the above embodiments, the inner tubular member includes a proximal end, a beveled gear disposed at the proximal end, a distal end, and an opening disposed at the distal end. In these embodiments, the inner tubular member may be configured to have an inner diameter (I.D.) of about 0.13 to about 0.23 inch, preferably about 0.15 to about 0.20 inch, even more preferably about 0.17 or 0.179 inch. It may be configured to have an outer diameter (O.D.) of about 0.15 to about 0.25 inch, preferably about 0.18 to about 0.22 inch, even more preferably about 0.19 or 0.198 inch. Its length may be configured to be about 15.00 to about 19.00 inch, preferably 16.00 to about 18.00 inch, even more preferably about 17.00 inch. The opening may be configured to have a length of about 0.20 to about 0.50 inch, preferably 0.30 to about 0.40 inch, even more preferably about 0.36, or about 0.37, or about 0.38 inch along its longitudinal axis. One side of the opening may be configured to have serrations, sharp teeth, knife edges, or other types of edges suitable for performing cutting functions. The serration, the tooth, or the knife edge of the opening has an outside surface edge and an inside surface edge. The inside surface edge may be preferably configured to be sharper than the outside surface edge for more efficient cutting purpose when aligned with the opening of the middle tubular member. Other sides may be configured to be smooth or other suitable edges. The beveled gear is configured to fully align with the engagement gear. It may be made whole with the inner tubular body, or it may be made separately and attached to the tubular body through means such as snap fit, screw tight, and high power glue known in the art. The inner tubular member is configured to synchronize with the middle tubular member to achieve tissue cutting along the middle axis line of the open window of the outer tubular member through means known in the art. The inner tubular member may be configured to be rotatable clockwise. The inner tubular member may be configured to be rotatable counter clockwise. The inner tubular member may be made of metal, stainless steel or other suitable materials strong enough for performing the desired functions. It may be made reusable, autoclavable, or disposable.

In the above embodiments, the engagement gear includes a gear head and a stem. The gear head is configured to be in full alignment with the beveled gear of the inner tubular member and the beveled gear of the middle tubular member. The gear head may be made by conventional means well known in the art. It may be made of metal, stainless steel or other suitable materials strong enough for performing the desired functions. It may be made reusable, autoclavable, or disposable. The engagement gear may be configured to be any suitable dimensions as feasible or convenient for a handpiece.

In the above embodiments, the medical device further comprises a handpiece. The handpiece may be configured to have a hand grip. In the above embodiments, the medical device further comprises an electrical motor. In the above embodiments, the medical device further comprises a handpiece and an electrical motor. The electrical motor may be a cannulated motor. The electrical motor may be disposed inside the handpiece. The electrical motor may be disposed outside of the handpiece. In the above embodiments, the handpiece may be made reusable, autoclavable, or disposable.

In all the above embodiments, it should understood that the connections, the sealing, and securing between the outer tubular member, the middle tubular member, the inner tubular member, and the engagement gear are achieved through the necessary support bearings, connectors, couplers, and other means known in the art. It should also be understood that the connections, the sealing, and securing between other components such as electrical motor, driveshaft, and motor control box may be similarly achieved.

In another embodiment, the present disclosure also provides a method of cutting tissue, the method comprising providing a medical device as described herein; inserting the medical device into a treatment site; positioning the medical device properly; turning on the device to cut tissue. Once the device is turned on, the opening of the middle tubular member and the opening of the inner tubular member constantly align with the open window of the outer tubular member to capture and cut the tissue. Once the device is power off, the distal end of the middle tubular member and the distal end of the outer tubular member form a closed configuration to keep the device safe for the patient.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

FIG. 1 is a partial schematic view of a medical device incorporating some features of the present disclosure. As shown in FIG. 1, the medical device 100 includes an outer tubular member 10, a middle tubular member 20, an inner tubular member 30, an engagement gear 40, and a handpiece 60. The medical device 100 also includes a cutting window region 8, which will be described in more detail in connection with FIG. 8. The middle tubular member 20 includes a beveled gear 23 at its proximal end. The middle tubular member 20 is received within the outer tubular member 10. The inner tubular member 30 includes a beveled gear 33 at its proximal end. The inner tubular member 30 is received within the middle tubular member 20. The inner tubular member 30 is configured to be attachable as shown by arrow 50 to a vacuum source (not shown). The engagement gear 40 engages with both the beveled gear 33 of the inner tubular member 30 and the beveled gear 23 of the middle tubular member 20. The engagement gear 40 is configured to be attachable as shown by arrow 70 through a flexible driveshaft 61 to a motor control box (not shown). The driveshaft 61 is housed inside the handpiece 60. The motor control box may be configured to control the rotation of the engagement gear 40 through the driveshaft in any desirable manner. In this embodiment, the engagement gear 40 is configured to be connectable to a power source. It should be understood that the connection between the driveshaft 61 and the engagement gear 40 may be accomplished through conventional coupling means well known in the art. Once powered, the engagement gear 40 will drive the inner tubular member 30 to rotate in one direction and drive the middle tubular member 20 to simultaneously rotate in an opposite direction through its interaction with the bevel gear 23 of the middle tubular member 20 and the beveled gear 33 of the inner tubular member 30. Even though not explicitly shown or labeled in FIG. 1, it should be understood that the connections, the sealing, and securing between/among the outer tubular member 10, the middle tubular member 20, the inner tubular member 30, the engagement gear 40, the handpiece 60, and the driveshaft 61 can be easily achieved through the necessary support bearings, connectors, couplers, and other mechanisms known in the art.

Figure 2:
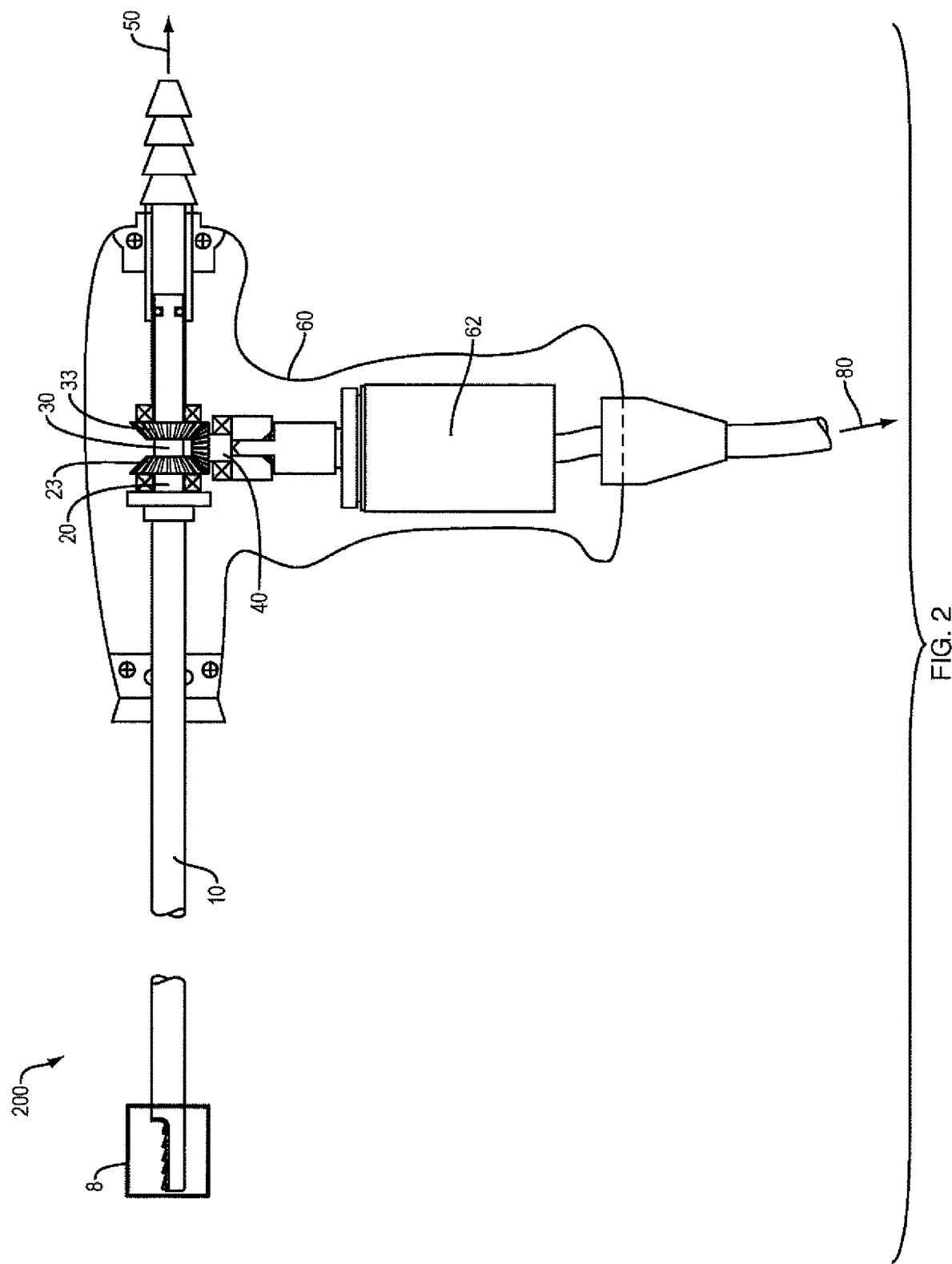
FIG. 2 is a partial schematic view of a medical device in accordance with another aspect of the present disclosure.

In accordance with another aspect of the present disclosure as shown in FIG. 2, the medical device 200 includes an outer tubular member 10, a middle tubular member 20, an inner tubular member 30, an engagement gear 40, and a handpiece 60. The medical device 200 also includes a cutting window region 8, which will be described in more detail in connection with FIG. 8. The middle tubular member 20 includes a beveled gear 23 at its proximal end. The middle tubular member 20 is received within the outer tubular member 10. The inner tubular member 30 includes a beveled gear 33 at its proximal end. The inner tubular member 30 is received within the middle tubular member 20. The inner tubular member 30 is configured to be attachable as shown by arrow 50 to a vacuum source (not shown). The engagement gear 40 engages with both the beveled gear 33 of the inner tubular member 30 and the beveled gear 23 of the middle tubular member 20. Different from a medical device shown in FIG. 1, the engagement gear 40 is instead configured to be attachable to an electrical motor 62. The electrical motor 62 is disposed inside the handpiece 60. The electrical motor is configured to be attachable through a cable to a power source (not shown) as shown by arrow 80. A controlling or processing device may be placed between the power source and the electrical motor 62 to monitor or control the rotation of the engagement gear in any desirable manner. It should be understood that the connection between the electrical motor 62 and the engagement gear 40 may be accomplished through the conventional coupling means well known in the art. Once connected to a power source through a cable line, the engagement gear 40 will drive the inner tubular member 30 to rotate in one direction and will drive the middle tubular member 20 to simultaneously rotate in an opposite direction through its interaction with the bevel gear 23 of the middle tubular member 20 and the beveled gear 33 of the inner tubular member 30. Even though not explicitly shown or labeled in FIG. 2, it should be understood that the connections, the sealing, and securing between/among the outer tubular member 10, the middle tubular member 20, the inner tubular member 30, the engagement gear 40, the handpiece 60, and the electrical motor 62 can be easily achieved through the necessary support bearings, connectors, couplers, and other mechanisms known in the art.

Figure 3:
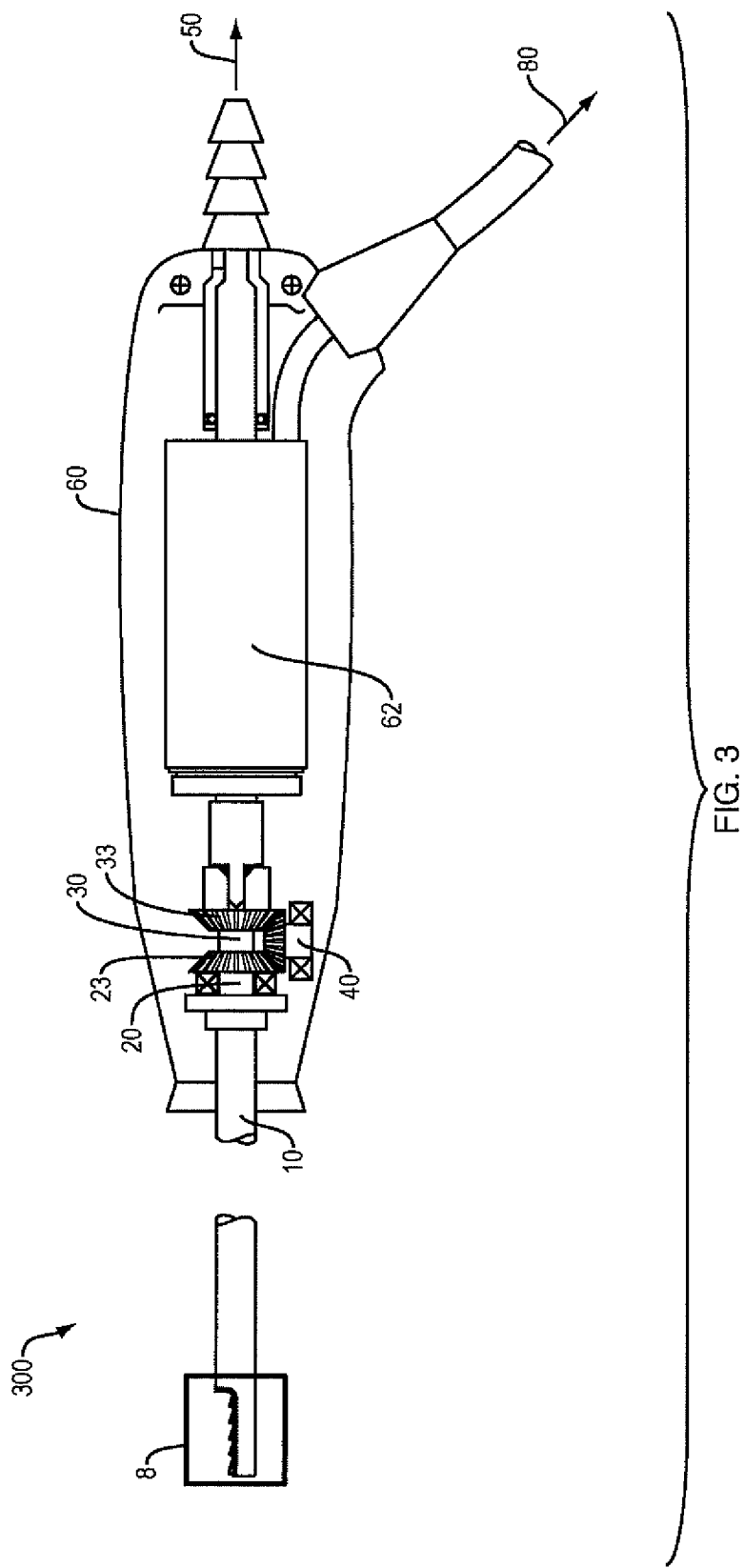
FIG. 3 is a partial schematic view of a medical device in accordance with yet another aspect of the present disclosure.

In accordance with yet a further aspect of the present disclosure as shown in FIG. 3, the medical device 300 includes an outer tubular member 10, a middle tubular member 20, an inner tubular member 30, an engagement gear 40, and a handpiece 60. The medical device 300 also includes a cutting window region 8, which will be described in more detail in connection with FIG. 8. The middle tubular member 20 includes a beveled gear 23 at its proximal end. The middle tubular member 20 is received within the outer tubular member 10. The inner tubular member 30 includes a beveled gear 33 at its proximal end. The inner tubular member 30 is received within the middle tubular member 20. Different from a medical device as shown in FIG. 1 or in FIG. 2, it is the inner tubular member 30 that is configured to be attachable to a cannulated electrical motor 62. The inner tubular member 30 is configured to be connectable, as shown by arrow 50, to a vacuum source (not shown) through the cannulated motor. The engagement gear 40 may be configured to be securely disposed inside the handpiece by any means known in the art. The engagement gear 40 is not directly connected to a power source. Rather, the beveled gear 33 of the inner tubular member 30 drives the engagement gear 40, which in turn drives the beveled gear 23 of the middle tubular member 20. As shown in FIG. 3, the cannulated electrical motor 62 may be configured to be in linear alignment with the inner tubular member to facilitate its suction function. However, other configurations may be contemplated. The cannulated electrical motor 62 may be configured to be attachable as shown by arrow 80 to a power source (not shown). A controlling or processing device may be placed between the power source and the electrical motor 62 to monitor or control the rotation of the engagement gear 40 in any desirable manner.

Figure 4:
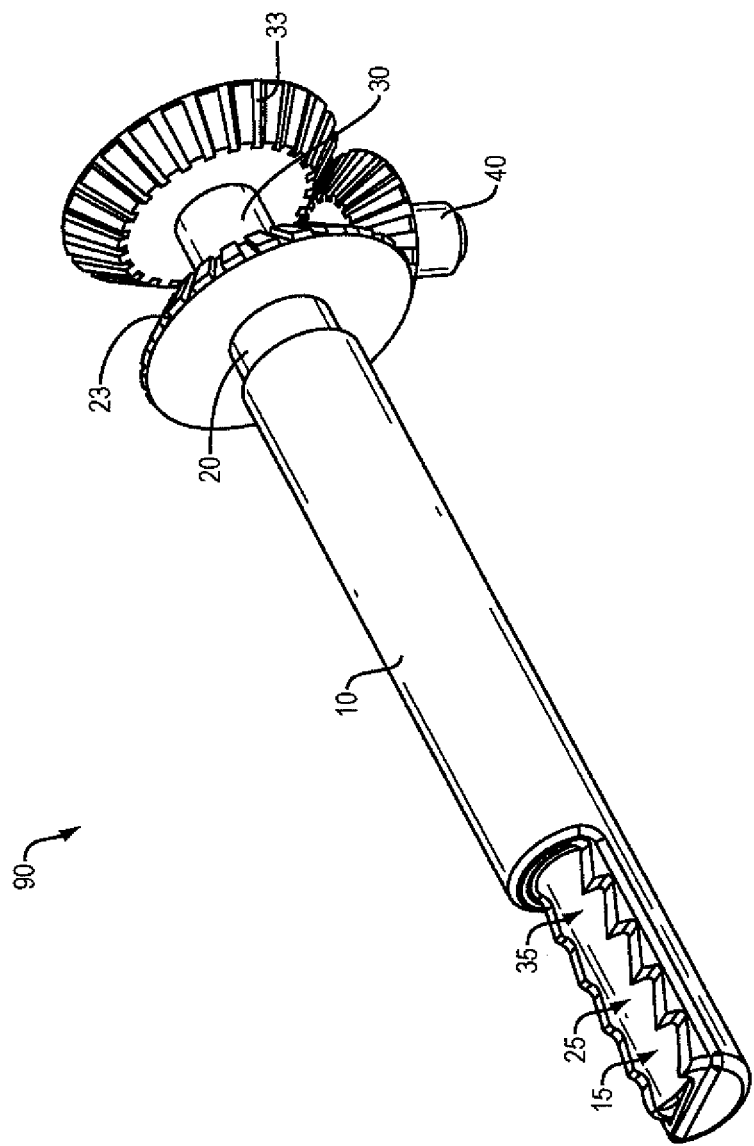
FIG. 4 is an isolated and enlarged perspective view of the blade assembly in an open configuration of a medical device in accordance with the present disclosure.

For the purpose of convenience, an outer tubular member, a middle tubular member, an inner tubular member and an engagement gear of a medical device in accordance with the present disclosure may be called a blade assembly of the medical device. FIG. 4 is a perspective view of such a blade assembly of a medical device of the present disclosure. As an embodiment shown in FIG. 4, the blade assembly 90 includes an outer hollow tubular member 10, a middle hollow tubular member 20, an inner hollow tubular member 30, and an engagement gear 40. The outer hollow tubular member 10 includes a proximal end, a distal end, and an open window 15 disposed at the distal end (referring to FIG. 6A for more details, infra). The middle hollow tubular member 20 includes a proximal end, a beveled gear 23 disposed at the proximal end, a distal end, and an opening disposed at the distal end (referring to FIG. 6B for more details, infra). The middle hollow tubular member 20 is received within the outer hollow tubular member 10. Part of the proximal end of the middle hollow tubular member 20 extends beyond the outer hollow tubular member for a disposition of the beveled gear 23. Consequently, the beveled gear 23 is disposed outside of the outer hollow tubular member 10. Alternatively put, the middle hollow tubular member 20 is partially received within the outer hollow tubular member 10. The beveled gear 23 may be configured to be any suitable size and dimension with just one requirement: capable of being in full and functional alignment with the engagement gear 40. The inner hollow tubular member 30 includes a proximal end, a beveled gear 33 disposed at the proximal end, a distal end, and an opening 35 disposed at the distal end (referring to FIG. 6C for more details, infra). The inner hollow tubular member 30 is received within the middle hollow tubular member 20. Part of the proximal end of the inner hollow tubular member 30 extends beyond the middle hollow tubular member 20 for a disposition of the beveled gear 33. Consequently, the beveled gear 33 is disposed outside of the middle hollow tubular member 20. Alternatively put, the inner hollow tubular member 30 is partially received within the middle hollow tubular member 20. As shown in FIG. 4, the opening 35 of the inner tubular member 30 and the opening 25 of the middle tubular member 20 are fully aligned or superimposed with the open window 15 of the outer tubular member 10. As a result, the blade assembly 90 is fully open under this configuration, and ready to capture and cut tissue (referring FIG. 8 for further information, infra).

Figure 5:
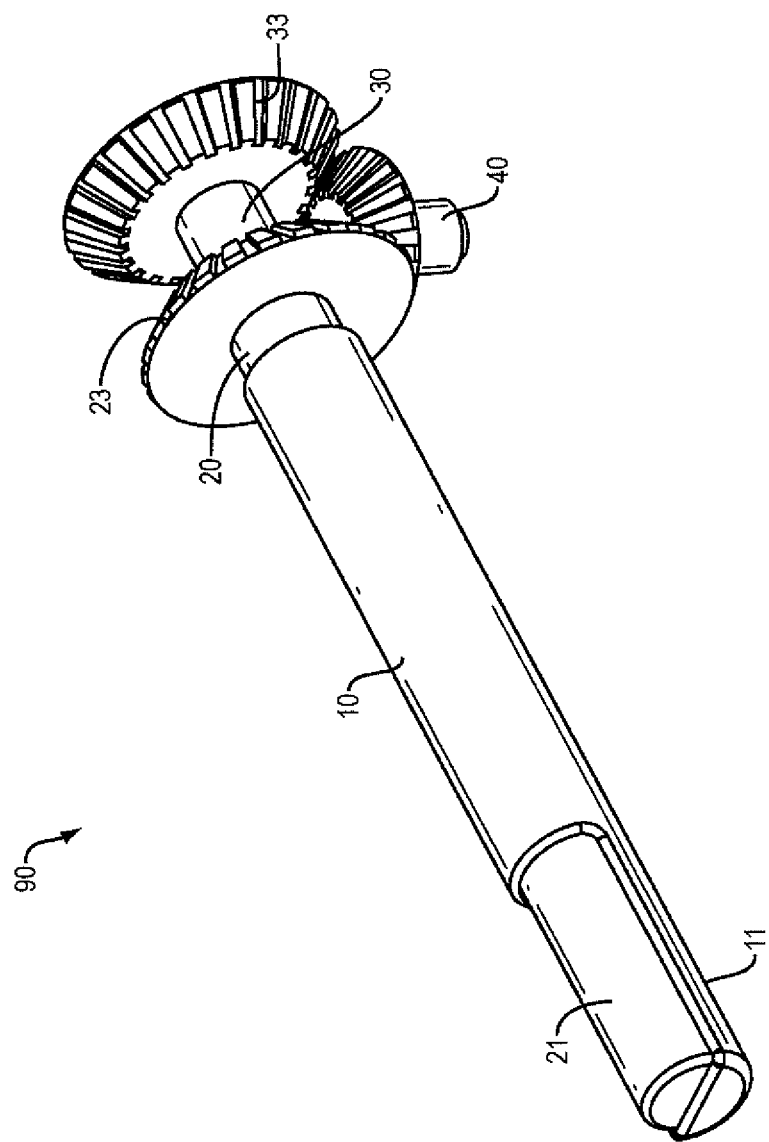
FIG. 5 is an isolated and enlarged perspective view of the blade assembly in a closed configuration of a medical device in accordance with the present disclosure.

FIG. 5 illustrates the blade assembly 90 in a closed configuration. As can be seen, the distal end 11 of the outer hollow tubular member 10 and the distal end 21 of the middle hollow tubular member 20 form a closed system such that no liquid can flow through the open window 15 of the outer tubular member 10 or the opening 25 of the middle hollow tubular member 20. Alternatively put, the blade assembly 90 is in a closed configuration to prevent any fluid from being sucked away from a treatment site. Moreover, the open window 15 of the outer tubular member 10 and the opening 25 of the middle tubular member 20 are configured to form a closed configuration whenever the medical device is not in use or power off to safeguard the device is safe to a patient or losing fluid unnecessarily. The blade assembly 90 alternates between the closed configuration and the open configuration to capture and cut tissue once the medical device is powered.

Figure 6A:
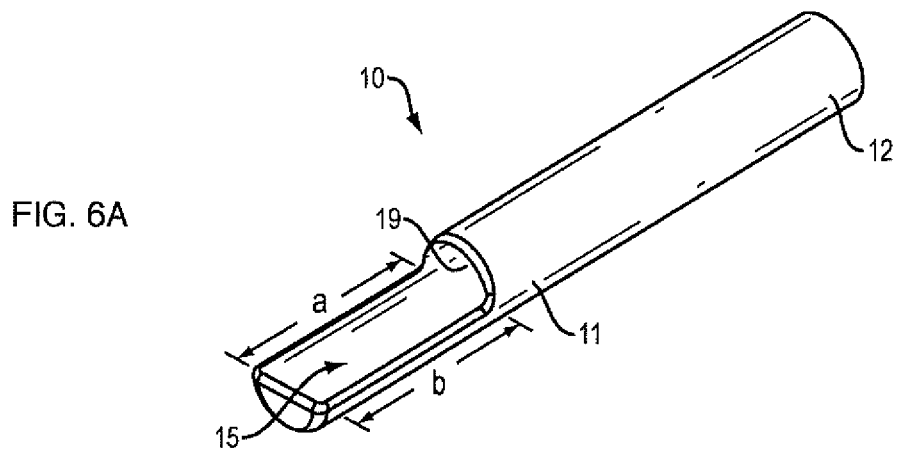
FIGS. 6A, 6B, and 6C show more detailed perspective views of the inner tubular member, the middle tubular member, and the outer tubular member, respectively, of a medical device in accordance with the present disclosure.

FIG. 6A is a perspective view of an outer hollow tubular member for a medical device of the present disclosure. The outer hollow tubular member 10 is configured to be stationary and fixed during operation and includes a proximal end 12, a distal end 11, and an open window 15 disposed at the distal end. Preferably, the open window 15 is disposed at the farthest end of the distal end so that it is easily accessible to the tissue to be cut. The edges 15a and 15b of the window 15 may be preferably configured to be smooth. However, any suitable edges may be contemplated. The lengths of 15a and 15b may each be preferably configured to be about 0.38 inch. The lengths of 15a and 15b may be preferably configured to be the same. The lengths of 15a and 15b may be configured to be slightly different. Other suitable length may be contemplated. The open area 19 may be vertical or sloped. Preferably, the circumferential edge of the open area 19 is configured to be smooth.

Figure 6B:
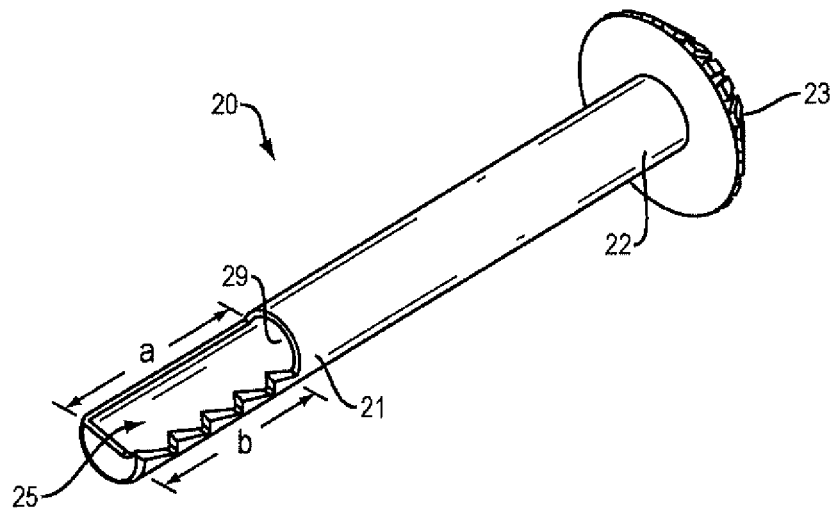

FIG. 6B is a perspective view of a middle hollow tubular member for a medical device of the present disclosure. The middle hollow tubular member 20 includes a proximal end 22, a beveled gear 23 disposed at the proximal end, a distal end 21, and an opening 25 disposed at the distal end. The beveled gear 23 may be made as one piece of the middle hollow tubular member by metal injection molding, or made as a separate piece and attachable to the middle tubular member by laser welding, screw tightening, snap fit, and high powered glue well known in the art. The opening 25 is configured to have one edge 25b with serrations, sharp teeth or knife type surface. The other edges may be configured to be smooth or other suitable edges. The lengths of 25a and 25b may each be preferably configured to be about 0.37 inch. The lengths of 25a and 25b may be preferably configured to be the same. The lengths of 25a and 25b may be configured to be slightly different. Other suitable length may be contemplated. The opening 25 is configured to be functionally alignable or superimposable with the open window 15 of the outer hollow tubular member 10. The open area 29 may be vertical or sloped. Preferably, the circumferential edge of the open area 29 is configured to be smooth.

Figure 6C:
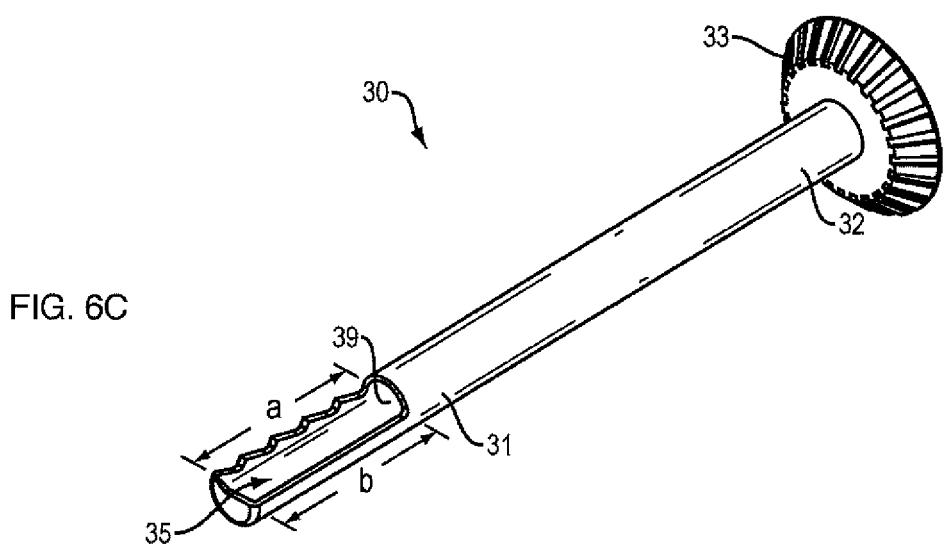

FIG. 6C is a perspective view of an inner hollow tubular member for a medical device of the present disclosure. The inner hollow tubular member 30 includes a proximal end 32, a beveled gear 33 disposed at the proximal end, a distal end 31, and an opening 35 disposed at the distal end. The beveled gear 33 may be made as one piece of the inner hollow tubular member 30 by metal injection molding, or made as a separate piece and attachable to the middle tubular member by laser welding, screw tightening, snap fit, and high powered glue well known in the art. The opening 35 is configured to have one edge 35a with serrations, sharp teeth or knife type surface. The other edges may be configured to be smooth or other suitable edges. The lengths of 35a and 35b may each be preferably configured to be about 0.36 inch. The lengths of 35a and 35b may be preferably configured to be the same. The lengths of 35a and 35b may be configured to be slightly different. Other suitable length may be contemplated. The opening 35 is configured to be in functional alignment or superimposition with the open window 15 of the outer hollow tubular member 10 such that the openings 25 and 35 are capable of capturing and cutting tissue. The open area 39 may be vertical or sloped. Preferably, the circumferential edge of the open area 39 is configured to be smooth.

Figure 7:
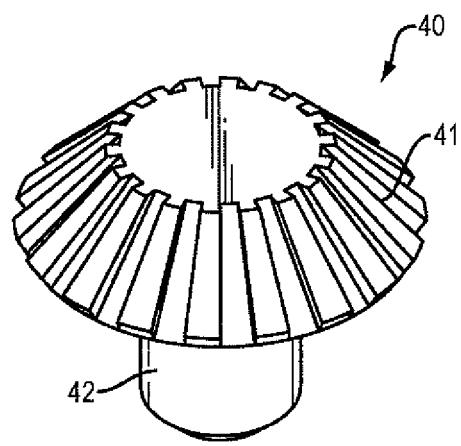
FIG. 7 shows an isolated and enlarged view of the engagement gear of a medical device in accordance with the present disclosure.

FIG. 7 is an isolated and enlarged view of an engagement gear for a medical device of the present disclosure. The engagement gear 40 includes a gear head 41 and a gear stem 42. The gear head 41 is such configured that it will properly and functionally align with the beveled gears of the inner tubular member and the middle tubular member. It may be made into any suitable dimensions and sizes. The gear stem 42 may also be made into any suitable dimensions and sizes. It may be configured to be connectable to a coupler or be properly secured inside a handpiece by means known in the art. The engagement gear 40 may be configured to be attachable to an electrical motor. It may also be configured to be functionally secured inside a handpiece by the conventional means known in the art. This way, the engagement gear is rotated through the beveled gear of the inner tubular member.

Figure 8:
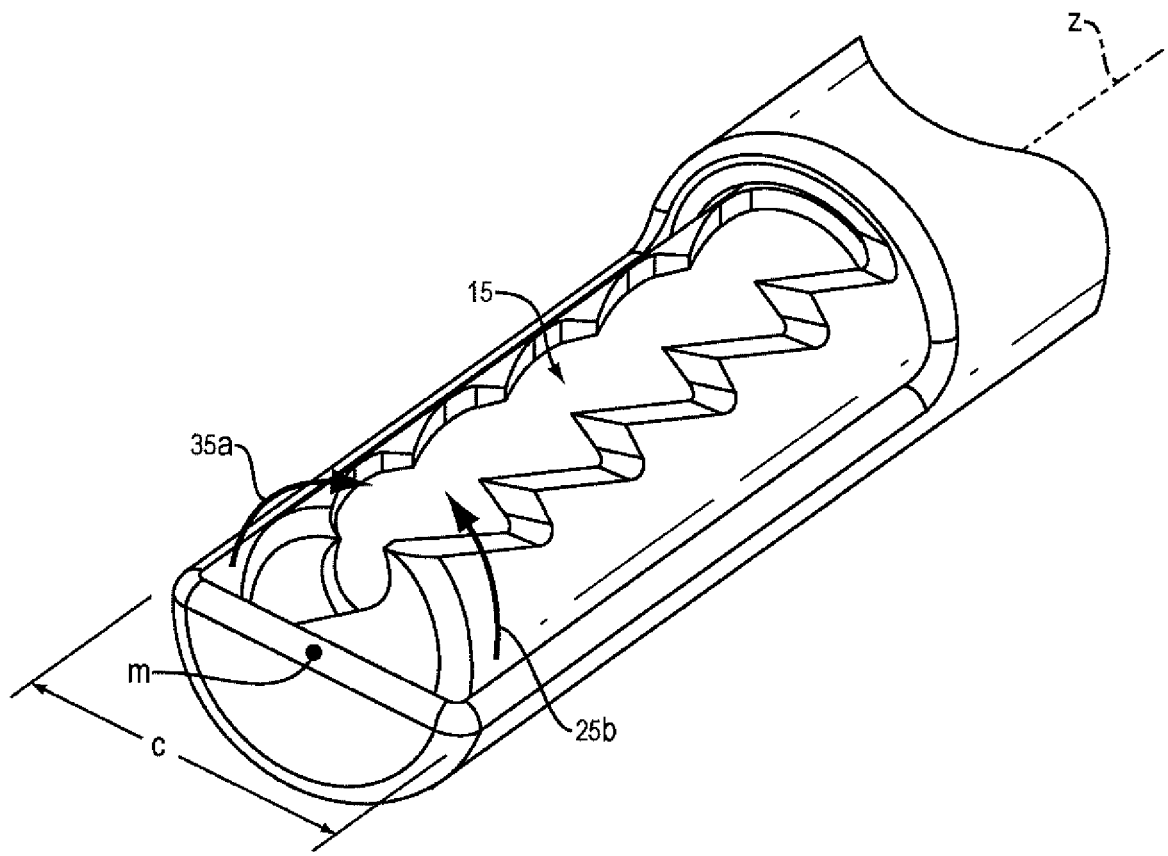
FIG. 8 shows an enlarged perspective view of the superimposition of the open window and the openings of the tubular members of a medical device in accordance with the present disclosure.

FIG. 8 is an enlarged view of the cutting window region of a medical device in accordance with the present disclosure. As can be easily identified, the opening of the inner tubular member and the opening of the middle tubular member are aligned with the open window of the outer tubular member to form a cutting tool. More particularly, when the serrated edge 25b of the middle tubular member 20 rotates around the longitudinal axis Z of the blade assembly towards the middle of the open window 15 (shown by 15m on edge 15c), the serrated edge 35a of the inner tubular member 30 also rotates around the Z axis towards the middle of the open window 15. It is preferably configured to make both the serrated edges simultaneously reach the middle of the open window 15 to ensure more efficient capturing and cutting of the exposed tissue. This synchronization can be easily achieved through suitable circuitry design and choice well known in the art. Other operating mechanisms/configurations may also be contemplated if necessary.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A medical device comprising:
an outer tubular member including an open window disposed at a distal end of the outer tubular member;
a middle tubular member configured to be received within the outer tubular member, the middle tubular member including a first opening disposed at a distal end of the middle tubular member and a first gear disposed at a proximal end of the middle tubular member;
an inner tubular member configured to be received within the middle tubular member, the inner tubular member including a second opening disposed at a distal end of the inner tubular member and a second gear disposed at a proximalmost end of the inner tubular member; and
a cannulated electrical motor configured to be attachable to a proximal end of the inner tubular member;
wherein the inner tubular member is configured to be rotatable in one direction while the middle tubular member is configured to be simultaneously rotatable in an opposite direction through engagement of a third gear with the first gear and the second gear; and
wherein the first opening and the second opening are configured to form a cutting tool when the inner tubular member and the middle tubular member rotate in opposite directions.

2. The medical device of claim 1, wherein the inner tubular member is configured to drive the middle tubular member.

3. The medical device of claim 1, wherein the second gear is configured to drive the third gear and the third gear is configured to drive the first gear.

4. The medical device of claim 1, wherein the inner tubular member is configured to be attachable to a suction source.

5. The medical device of claim 1, wherein the medical device further comprises a handpiece.

6. The medical device of claim 5, wherein the cannulated electrical motor is disposed inside the handpiece.

7. The medical device of claim 1, wherein the first gear includes a first beveled gear and the second gear includes a second beveled gear.

8. The medical device of claim 1, wherein the distal end of the middle tubular member forms a closed configuration with the distal end of the outer tubular member when the inner tubular member and the middle tubular member are not rotating.

9. A medical device comprising:
- an outer tubular member having an open window disposed at a distal end of the outer tubular member;
- a middle tubular member configured to be received within the outer tubular member and having a first gear and a first opening, the first opening disposed at a distal end of the middle tubular member and the first gear disposed at a proximal end of the middle tubular member;
- an inner tubular member configured to be received within the middle tubular member and having a second gear and a second opening, the second opening disposed at a distal end of the inner tubular member and the second gear disposed at a proximalmost end of the inner tubular member; and
- a cannulated electrical motor configured to be attachable to a proximal end of the inner tubular member, the cannulated electrical motor defining a fluid conduit that is in fluid communication with the proximal end of the inner tubular member;
- wherein the inner tubular member is configured to be rotatable in one direction while the middle tubular member is configured to be simultaneously rotatable in an opposite direction through engagement of an engagement gear with the first gear of the middle tubular member and the second gear of the inner tubular member; and
- wherein the first opening and the second opening are configured to form a cutting tool when the inner tubular member and the middle tubular member rotate in opposite directions.

10. The medical device of claim 9, wherein the engagement gear, the first gear, and the second gear are bevel gears.

11. The medical device of claim 9, wherein the inner tubular member is configured to be attachable to a suction source via the fluid conduit of the cannulated electrical motor.

12. The medical device of claim 9, wherein the medical device further comprises a handpiece.

13. The medical device of claim 12, wherein the cannulated electrical motor is disposed inside the handpiece.

14. The medical device of claim 13, wherein the cannulated electrical motor is in linear alignment with the inner tubular member.

15. The medical device of claim 9, wherein the distal end of the middle tubular member forms a closed configuration with the distal end of the outer tubular member when the inner tubular member and the middle tubular member are not rotating.

* * * * *